(12) United States Patent
Gustavsson

(10) Patent No.: US 9,943,664 B2
(45) Date of Patent: Apr. 17, 2018

(54) TEMPORARILY FOLDABLE CATHETER ASSEMBLY

(71) Applicant: DENTSPLY IH AB, Molndal (SE)

(72) Inventor: Evelina Gustavsson, Onsala (SE)

(73) Assignee: DENTSPLY IH AB, Mölndal (SE)

( * ) Notice: Subject to any disclaimer, the term of this patent is extended or adjusted under 35 U.S.C. 154(b) by 275 days.

(21) Appl. No.: 13/714,621

(22) Filed: Dec. 14, 2012

(65) Prior Publication Data

US 2013/0161227 A1 Jun. 27, 2013

Related U.S. Application Data

(60) Provisional application No. 61/580,472, filed on Dec. 27, 2011.

(30) Foreign Application Priority Data

Dec. 27, 2011 (EP) .................................... 11195739

(51) Int. Cl.
*B65D 81/26* (2006.01)
*A61M 25/00* (2006.01)

(52) U.S. Cl.
CPC ....... *A61M 25/002* (2013.01); *A61M 25/0017* (2013.01)

(58) Field of Classification Search
CPC .......... A61M 25/002; A61M 25/0017
USPC ........ 206/210, 364, 365, 438, 571; 604/328, 604/544
See application file for complete search history.

(56) References Cited

U.S. PATENT DOCUMENTS

| | | |
|---|---|---|
| 3,035,691 A | 5/1962 | Rasmussen et al. |
| 3,761,013 A | 9/1973 | Schuster |
| 3,967,728 A | 7/1976 | Gordon et al. |
| 4,552,269 A | 11/1985 | Chang |
| 4,568,334 A | 2/1986 | Lynn |
| D300,947 S | 5/1989 | Utas-Sjoberg |
| 4,923,061 A | 5/1990 | Trombley, III |
| D311,064 S | 10/1990 | Utas-Sjoberg |
| D325,526 S | 4/1992 | Deguchi et al. |
| 5,163,554 A * | 11/1992 | Lampropoulos .... A61M 25/002 206/363 |
| 5,226,530 A * | 7/1993 | Golden ............... A61M 25/002 206/210 |

(Continued)

FOREIGN PATENT DOCUMENTS

| | | |
|---|---|---|
| EP | 0217771 B1 | 12/1991 |
| EP | 2072075 A1 | 6/2009 |

(Continued)

OTHER PUBLICATIONS

European Search Report, Application No. 11195739.5, Publication May 24, 2012.

(Continued)

*Primary Examiner* — Luan K Bui
(74) *Attorney, Agent, or Firm* — Perkins Coie LLP

(57) ABSTRACT

A catheter assembly is disclosed, comprising a catheter and an elongate package accommodating said catheter in a closed condition. The package is provided with an insert opening arranged to releasably receive an end of the elongate package in the closed condition, thereby temporarily retaining said closed package in a folded disposition in which also the catheter is folded.

20 Claims, 5 Drawing Sheets

(56) References Cited

U.S. PATENT DOCUMENTS

| | | | |
|---|---|---|---|
| 5,309,604 A * | 5/1994 | Poulsen | A61M 5/1418 24/16 R |
| 5,330,464 A | 7/1994 | Mathias et al. | |
| 5,344,011 A * | 9/1994 | DiBernardo et al. | 206/364 |
| 5,366,444 A * | 11/1994 | Martin | A61M 25/09041 242/405 |
| 5,407,070 A | 4/1995 | Bascos | |
| D364,491 S | 11/1995 | Bradfield et al. | |
| 5,848,691 A * | 12/1998 | Morris | A61M 25/002 206/364 |
| 5,895,374 A | 4/1999 | Rodsten | |
| 6,409,717 B1 * | 6/2002 | Israelsson et al. | 604/544 |
| 6,594,971 B1 | 7/2003 | Addy et al. | |
| D499,643 S | 3/2004 | Nestenborg | |
| D490,302 S | 5/2004 | Nestenborg | |
| D491,803 S | 6/2004 | Nestenborg | |
| D496,266 S | 9/2004 | Nestenborg | |
| D498,671 S | 11/2004 | Nestenborg | |
| D498,672 S | 11/2004 | Nestenborg | |
| D499,016 S | 11/2004 | Nestenborg | |
| D499,017 S | 11/2004 | Nestenborg | |
| D499,335 S | 12/2004 | Nestenborg | |
| 6,849,070 B1 * | 2/2005 | Hansen et al. | 604/544 |
| D503,335 S | 3/2005 | Risberg et al. | |
| D505,067 S | 5/2005 | Nestenborg | |
| D534,649 S | 1/2007 | Haga et al. | |
| 7,476,223 B2 | 1/2009 | McBride | |
| D595,842 S | 7/2009 | Haga et al. | |
| D610,445 S | 2/2010 | Kedem | |
| 7,770,726 B2 | 8/2010 | Murray et al. | |
| D623,535 S | 9/2010 | Nilsson et al. | |
| 7,823,722 B2 | 11/2010 | Bezou et al. | |
| 7,857,770 B2 * | 12/2010 | Raulerson | A61M 25/0105 600/585 |
| 8,052,673 B2 | 11/2011 | Nestenborg | |
| D699,559 S | 2/2014 | Gustavsson | |
| D734,165 S | 7/2015 | Kearns et al. | |
| D746,152 S | 12/2015 | Murray et al. | |
| D747,184 S | 1/2016 | Murray et al. | |
| D752,452 S | 3/2016 | Kearns et al. | |
| D764,943 S | 8/2016 | Murray et al. | |
| D775,522 S | 1/2017 | Gustavsson | |
| 2001/0001443 A1 | 5/2001 | Kayerod et al. | |
| 2002/0130059 A1 * | 9/2002 | Armijo | A61M 25/002 206/438 |
| 2003/0055403 A1 | 3/2003 | Nestenborg et al. | |
| 2003/0083644 A1 * | 5/2003 | Avaltroni | 604/544 |
| 2003/0168365 A1 | 9/2003 | Kaern | |
| 2005/0061698 A1 * | 3/2005 | Delaney | A61M 25/002 206/364 |
| 2005/0070882 A1 * | 3/2005 | McBride | 604/544 |
| 2005/0178684 A1 * | 8/2005 | Kesler | A61M 25/002 206/364 |
| 2006/0186010 A1 * | 8/2006 | Warnack | A61M 25/002 206/438 |
| 2006/0278546 A1 * | 12/2006 | State et al. | 206/364 |
| 2006/0278547 A1 * | 12/2006 | Rowe et al. | 206/364 |
| 2006/0289336 A1 | 12/2006 | Ford | |
| 2008/0051763 A1 * | 2/2008 | Frojd | 604/544 |
| 2008/0183181 A1 * | 7/2008 | Treacy | A61L 2/206 606/108 |
| 2008/0200907 A1 | 8/2008 | Nestenborg | |
| 2009/0163884 A1 * | 6/2009 | Kull-Osterlin | A61M 25/002 604/328 |
| 2009/0200186 A1 | 8/2009 | Nestenborg et al. | |
| 2011/0056852 A1 | 3/2011 | Frojd | |
| 2011/0114520 A1 | 5/2011 | Matthison-Hansen | |
| 2011/0295239 A1 | 12/2011 | Gustavsson | |
| 2012/0037525 A1 * | 2/2012 | Peck | A61L 2/206 206/364 |
| 2012/0165790 A1 | 6/2012 | Gustavsson et al. | |
| 2012/0172846 A1 * | 7/2012 | Nakamoto | A61M 25/002 604/533 |
| 2012/0181193 A1 * | 7/2012 | Wu | A61F 2/0095 206/204 |
| 2012/0261290 A1 * | 10/2012 | Limjaroen | A61M 25/002 206/364 |
| 2013/0006226 A1 * | 1/2013 | Hong et al. | 604/544 |

FOREIGN PATENT DOCUMENTS

| | | |
|---|---|---|
| EP | 2106821 A1 | 10/2009 |
| EP | 2292293 A1 | 3/2011 |
| EP | 2389972 | 11/2011 |
| JP | 63-38470 | 2/1988 |
| JP | 3-501570 | 4/1991 |
| JP | 2001500414 | 1/2001 |
| JP | 2011139882 A | 7/2011 |
| WO | 1989004685 | 6/1989 |
| WO | 1998011932 | 3/1998 |
| WO | 2010006620 A1 | 1/2010 |
| WO | 2011058397 | 5/2011 |

OTHER PUBLICATIONS

Office Action for Japanese Patent Application No. 2014-549436, dated Dec. 6, 2016 (10 pages).

Office Action for Chinese Patent Application No. 201280055819.7, dated Sep. 27, 2016 (12 pages).

Office Action for Japanese Patent Application No. 2014-549436, dated Oct. 10, 2017, with translation (10 pages).

European Search Report, Application No. 11195736.1, Search completed May 10, 2012.

* cited by examiner

TEMPORARILY FOLDABLE CATHETER ASSEMBLY

RELATED APPLICATIONS

This patent application claims the benefit of and priority to EP Application Ser No. 11195739.5, filed on Dec. 27, 2011 and U.S. Provisional Patent Application Ser. No. 61/580,472, filed on Dec. 27, 2011, which are herein incorporated by reference for all purposes.

TECHNICAL FIELD

The present invention relates to a catheter assembly comprising a catheter, and preferably a urinary catheter, and an elongate package accommodating the catheter. Specifically, the invention pertains to a catheter having a hydrophilic surface coating, wherein the assembly also includes a wetting fluid for activation of the hydrophilic surface coating.

BACKGROUND OF THE INVENTION

The present invention relates to a catheter assembly, and in particular for urinary hydrophilic catheters. Catheters are commonly used for draining bodily fluids, e.g. from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

However, there is still a need for improved packages for such catheter assemblies. The package should preferably be relatively simple and cost-efficient to produce. Further, the package should be easy to handle, even for users with reduced dexterity. Still further, the package should enable adequate wetting of the catheter and handling of the package in a clean manner. The package should also preferably be rather small, so that it can easily be carried around by the user in his/hers daily life. It would also be highly advantageous if the package is resealable, so that the catheter could be re-closed after use, if it cannot be immediately disposed of.

Patent application US 2011/056852 by the same applicant discloses a urinary catheter assembly having a resealable opening. However, even though this catheter assembly is highly usable for short catheters, for female users, re-insertion of longer catheters, typically for male users, may be cumbersome and with the risk of spillage and the like. Male catheters may be 40 cm long, or even longer, and insertion of the tip portion through the resealable opening without touching the insertable part of the catheter is rather difficult, especially for users with reduced dexterity. Further, even though this product is small when used for short female catheters, it inevitably becomes much longer when used for long male catheters. Further, closing of the reseable opening after re-insertion of the catheter in a sufficiently sealed manner may also be difficult with this known catheter assembly, and again, especially for users with reduced dexterity.

Since a catheter needs to be of sufficient length to extend through the urethra, for instance having an insertable length of at least 200-350 mm for male users, the catheter assembly generally requires more space than is convenient. The assembly may thus be cumbersome to store, transport and handle, which is inconvenient not least for the individuals for whom catherisation is a daily-life procedure. To alleviate the inconvenience, there is a strive for less space consuming catheter assemblies which improve life quality for the user of catheters in that the assemblies can be handled and stored more discreetly, for instance in the pocket of a users clothing. Various attempts to produce more compact catheter assemblies have been made.

For example, US 2009/163884 by the same applicant discloses a catheter assembly including a urine collection bag integrated in a rearward part of the package. This assembly is made more compact by folding the rearward part over an elongate pocket housing the catheter. However, even though this solution makes the catheter assembly significantly more compact, the size of the product is still at least as long as the catheter itself.

A similar approach is taken in U.S. Pat. No. 8,052,673, also by the same applicant, in which a rearward part of the package housing the wetting fluid container is folded over a forward part housing the catheter. The folded parts are held together by means of an adhesive. However, even though this solution also makes the catheter assembly significantly more compact, the size of the product is still at least as long as the catheter itself.

There have also been attempts to make the catheter telescopic, but for natural reasons, such solutions are difficult and costly to produce.

Still further, it has been proposed to arrange the catheter in a curved disposition. For example, EP 2 106 821 by the same applicant discloses a catheter assembly in which the package comprises pleated regions allowing the package, and the catheter within it, to be arranged in a folded or double folded disposition. This solution greatly reduces the size of the catheter assembly. However, this type of package is relatively complicated and costly to produce. Still further, even though the curving of the catheter is arranged to exceed a minimum diameter of curvature, there is still a risk that the catheter will remain in a curved disposition even when withdrawn from the package. This is due to the fact that catheters are normally of a material having certain rigidity/shape memory characteristics. Storing the catheter assembly for a long period of time in a non-straight disposition, may result in kinking and distortion of the catheter, and imply resistance of easily reverting the catheter to its straight disposition prior to an intended use. The user may subsequently experience discomfort during insertion of the catheter, especially if the first section of the insertable part remains in a non-straight disposition.

Consequently, there is a need for a leaner and less bulky catheter assembly, and/or a catheter assembly which is less expensive to produce, meanwhile easy and convenient to handle and store, and in which the catheter will assume as straight a disposition as desired before use.

SUMMARY OF THE INVENTION

It is therefore an object of the present invention to provide a catheter assembly and a method which at least alleviate the above-discussed problems.

This object is obtained by means of a catheter assembly and a method in accordance with the appended claims.

According to a first aspect of the invention there is provided a catheter assembly comprising a catheter, preferably a urinary catheter, and an elongate package accommodating said catheter in a closed condition, wherein the package is provided with an insert opening arranged to releasably receive an end of the elongate package in said closed condition, thereby temporarily retaining said closed package in a folded disposition in which also the catheter is folded.

The present invention is based on the realization by the inventor that the compact state is most required during limited periods of time, e.g. when the user is to bring a catheter assembly along for during certain activities or trips. However, the significant length of the catheter assembly when the catheter is handled during manufacturing, storage, etc, would normally not be a problem, since many catheter assemblies of this type are any way stored together in relatively large boxes for transportation and storage. The present invention is further based on the realization that shape deformation due to memory in the material will not occur, or only occur to a very limited extent, if a curved shape is only maintained for a limited period of time, such as for a few hours or a few days. Further, it also gives the user a freedom to determine by himself how to use the catheter assembly, and to which extent deformations should be avoided. Thus, users being very sensitive to non-straight catheters may restrict the use of the folded disposition to very short times, or avoid it altogether, whereas less sensitive users may use the folded disposition for a much longer time period.

By means of the present invention, the user can himself easily arrange the catheter assembly in a compact state, without opening the package, for temporary storage in a compact state, e.g. in a pocket, a small bag or the like.

This functionality is rendered possible in a very efficient way by means of the provision of an insert opening in the package, in which an end of the catheter can be releasably received after folding of the package, and the catheter within it. Hereby, the compact state is efficiently maintained, and is also easy to release when the catheter assembly is about to be used. The compact state can also easily be released for continued long time storage.

Since the catheter is only maintained in curved disposition for limited period(s) of time, no shape deformation etc will occur.

Further, the releasable folding of the catheter assembly in this way requires very limited modifications to the catheter assembly, which means that the catheter assembly can be produced in a very cost-efficient manner.

By "temporary" and "temporarily" is in the context of this application meant a state maintained for a limited period of time, said limited time period being only a few hours or a few days. Preferably, this includes a time range of 0-48 hours, and most preferably a time range of 0-24 hours.

By "elongate package" is in the context of this application meant that the width of the package at all places is significantly smaller than the length of the package.

The insert opening may be provided in various ways, e.g. by forming an open-ended pocket in the package, or by arranging a strap on the package, with a loop forming the insert opening. However, in a preferred embodiment, the insert opening is formed as a slit opening in the package. Formation of such a slit opening is easy to obtain during manufacturing, and requires no or very limited amounts of extra material. Most preferably, the slit opening is formed in a tab area on a side of said package. Hereby, the slit opening is formed separated from the compartment housing the catheter, which ensures that the integrity of the compartment is maintained.

It is further preferred that the insert opening is arranged to receive the end of the package housing the insertable end of the catheter. Most conveniently, this is obtained by arranging the insert opening at, e.g. overlying, or close to the rearward part of the package, housing the non-insertable rearward part of the catheter.

The insert opening is preferably dimensioned to narrowly surround a received end of the package. Hereby, an inserted end of the package is efficiently maintained in the compact state only by friction between the insert opening and the received end. However, further means for ensuring that the inserted end is maintained in its desired position may be provided. For example, a material with relatively high surface friction may be used at certain positions, or in the entire package. It is further possible to provide roughened or textured portions at the insertable end. Further, additionally or alternatively, the inserted end may be slightly larger than the adjacent part of the package, which is not intended to be inserted. This slight enlargement may be obtained through a slight width increase at the end, by one or several protrusions formed in the inserted end, or the like.

As already mentioned, the package can easily be produced in a variety of ways, comprising e.g. a package formed entirely or partly by a tube. However, in a preferred embodiment, the package is formed of two sheets of foil material being joined along the edges of the foils, thereby forming a closed compartment therein for housing said catheter. Preferably, the insert opening is then arranged in a part of the package not forming said compartment.

Most preferably, a first of said foils has been deep drawn into a trough shape, the package further comprising a resealable opening arranged within the bounds of the second foil.

In the context of the present application, "resealing" relates to closure of a previously opened opening, wherein the closure forms closure that at least to a large extent prevents liquid from leaking out from the closure.

In the context of the present application, "deep drawn" defines any process forming a permanent deformation of a plastic material, such as vacuum forming and other types of thermoforming by means of heating, and the like. In a preferred embodiment, vacuum forming is used. In vacuum forming, the sheet is heated to a forming temperature, stretched onto or into a single-surface mold, and held against the mold by applying vacuum between the mold surface and the sheet. The mold may e.g. be a cast or machined aluminum mold, or a composite mold.

In the context of the present application, "trough" defines a shape having a rim, thin or wide, encircling a lowered middle section.

The rim is preferably provided with an essentially planar edge portion, encircling the lowered middle section. The depth of the lowered middle section is preferably sufficient to entirely accommodate the height of the catheter and/or the height of a wetting fluid container. Preferably, the depth is in the range 0.2-3 cm, and preferably in the range 0.5-2 cm, and most preferably in the range 0.7-1.5 cm. It is further possible to have different depths in different parts of the package. For example, a part housing the non-insertable catheter end, and optionally a wetting fluid container, may have a greater depth than a part housing the insertable part of the catheter.

The second foil is preferably not deep-drawn. Instead, this foil is preferably essentially planar, or only slightly curved.

This package is very well suited for use for hydrophilic catheters, i.e. catheters being provided with a hydrophilic surface coating or catheters being made of a hydrophilic material. The package enables easy, clean and efficient wetting and handling of the hydrophilic catheter, and also provides sterile conditions for the entire wetting process. At the same time the package is relatively simple and cost-efficient to produce. In particular, the catheter assembly is well-suited for the type of assemblies including a hydrophilic catheter and a wetting fluid being accommodated by the package. The wetting fluid may e.g. be arranged directly in contact with the hydrophilic surface of the catheter, or in a separate compartment of the package or in a separate container being housed by the package.

Since the resealable opening is arranged in a non-deep drawn, and preferably essentially planar, sheet, opening and re-closing of the resealable opening is greatly facilitated. It has been found by the present inventor that re-arranging a resealable opening into a sealed and sufficiently closed condition is much simpler on a planar or only slightly curved surface than on surfaces curved in one or several directions. This is particularly advantageous for users having reduced dexterity.

Further, during manufacturing, formation of the resealable opening is also facilitated, enabling a more cost-efficient production.

Still further, since the first sheet underlying the second sheet with the resealable opening is deep drawn into a trough shape, a spacing between the first and second sheets are formed and continuously maintained. This spacing essentially corresponds to the depth of the lowered middle section of the deep drawn trough. Hereby, it is avoided that the catheter deforms the second sheet to any significant degree. It is further ensured that there is a spacing between the sheets also after withdrawal of the catheter from the package. This greatly facilitates re-insertion of the catheter, since re-insertion of the catheter hereby does not necessitate separation of the sheets. Instead, the catheter may simply be guided through the resealable opening into the already available compartment formed between the sheets. This is particularly advantageous for use with relatively long catheters, when manipulation of the tip portion of the catheter by holding the rearward connector end is complicated if it involves any other actions than simply guiding the tip into a preformed compartment of sufficient dimensions. Further, this simplified re-insertion is highly advantageous for users with reduced dexterity.

The two sheets of foil material are preferably joined along the edges of the foils, and preferably connected around the edges by means of welding. Preferably, the first and second sheet materials comprise laminated sheets, having a weldable inner layer and a protective outer layer.

The resealable opening is preferably arranged at, and preferably overlying, the part of the package housing the non-insertable, rearward end of the catheter. Hereby, the catheter may be withdrawn with the connector end first, which enables a clean and convenient way of handling the catheter without touching the insertable part directly by hand.

Preferably, the resealable opening is arranged as a peel opening. Most preferably, the resealable opening in the second sheet may comprise a perforation line extending along a non-closed loop in one of said sheets, said perforation line defining a flap opening, and a third sheet connected by means of an adhesive over said flap opening, wherein said third sheet with a margin covers the entire flap opening.

The third sheet further preferably forms a tab not provided with adhesive, said tab providing a grip portion for peel opening of the package.

By "perforation" is meant a diminished material thickness, possibly extending over the entire thickness, providing a complete cut-through. By means of "perforation line" is meant a line with continuous or discontinuous perforations. Thus, in the context of the present application, "perforation line" is used to indicate a line forming a weakening, such as a total cut-through, a partial cut-through, point perforations, or the like, forming a weakening where a rupture will occur when a force is exerted on the material.

Such a resealable opening is efficient and easy to use, and also relatively simple to produce. The tab enables a very simple peel-opening of the package. At the same time, the flap opening provides an efficient way of removing the catheter, and also for resealing of the package, once the catheter has been used and been replaced in the package.

In production, one of the first and second sheets may be provided with the non-closed loop perforation line, by means of cutting or the like, and the third sheet material can thereafter be adhered on top of it. Alternatively, the third sheet material can be added first and the perforated line (or total cut) could be formed afterwards.

The adhesive is preferably adapted to maintain a sterile closure of the package before use, and to be resealable after use.

The non-closed loop defining the flap opening preferably debouches towards (i.e. faces) the end of the package housing the insertion end of the catheter. Hereby, the tab is arranged close to the end of the package, and the peeling occurs downwards, towards the insertion end of the catheter, which is efficient for avoiding spillage of the wetting fluid within the package after activation, especially when the catheter assembly is hanged, adhered or otherwise arranged in a vertical direction during withdrawal from the package and re-insertion into the package.

The package is elongate, and preferably narrowly surrounding the catheter and the optional wetting fluid compartment. For example, the package may have an essentially rectangular form in the forward section, and a larger and also essentially rectangular form in the rearward section. Hereby, a very cost-efficient and compact product is obtained.

Preferably, the catheter is a hydrophilic urinary catheter for intermittent use. However, even though the catheter assembly is at present primarily intended for urinary hydrophilic catheters, where the package also includes a wetting fluid, the catheter assembly may also be used for other types of catheters. For example, the catheter may be other types of catheters, such as vein catheters and the like. Further, the catheter may be provided with other types of lubricious coatings, such as gel lubricants and the like, or being without any surface coating at all. Still further, assemblies without a wetting fluid are also feasible.

Most preferably, the wetting fluid is arranged separately from said catheter in said package, and preferably being arranged in a wetting fluid container arranged within said package, and wherein the insert opening is arranged in the vicinity of said wetting fluid container. The separate arrangement of the wetting fluid can be obtained by means of closed compartment within the package. However, in a preferred embodiment, the wetting fluid is arranged in a wetting fluid container arranged within said package, such as in a pouch, sachet or the like. In case the wetting fluid is arranged separately, the container or compartment is openable into the part of the package housing the catheter, in order to enable release of the wetting fluid into contact with the hydrophilic part of the catheter before use. Release of the wetting fluid can be obtained by squeezing, bending or the like, as is per se well known in the art.

The wetting fluid container is preferably arranged in a wider rearward part of the package, also accommodating the rearward, non-insertable end of the catheter, and wherein the package further comprises an elongate forward part narrowly accommodating the insertable end of the catheter, whereby the elongate forward part is foldable around said wider rearward part.

The closed package in its folded disposition preferably comprises at least one fold, and preferably at least two folds, and most preferably at least three folds.

In the folded disposition, it is preferred that a maximum length of said catheter assembly is less than half a length of said catheter in a straight disposition, and preferably about a third of said catheter length.

The length of said catheter, in unfolded state, preferably exceeds 200 mm, and preferably exceeds 300 mm.

According to a second aspect of the invention, there is provided a method of temporarily bringing a catheter assembly to a compact state, said catheter assembly comprising a catheter accommodated in an elongate catheter package in a closed condition, comprising the steps:

folding a part of the package over another part of the package; and inserting an end of the elongate package in said closed condition into an insert opening in said package, thereby temporarily retaining said closed package in a folded disposition in which also the catheter is folded.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIGS. 3A and 3B illustrate intermediate folding steps, and FIGS. 3C and 3D illustrate the folded catheter assembly from above and below.

DETAILED DESCRIPTION OF THE PREFERRED EMBODIMENTS

Figure 1:
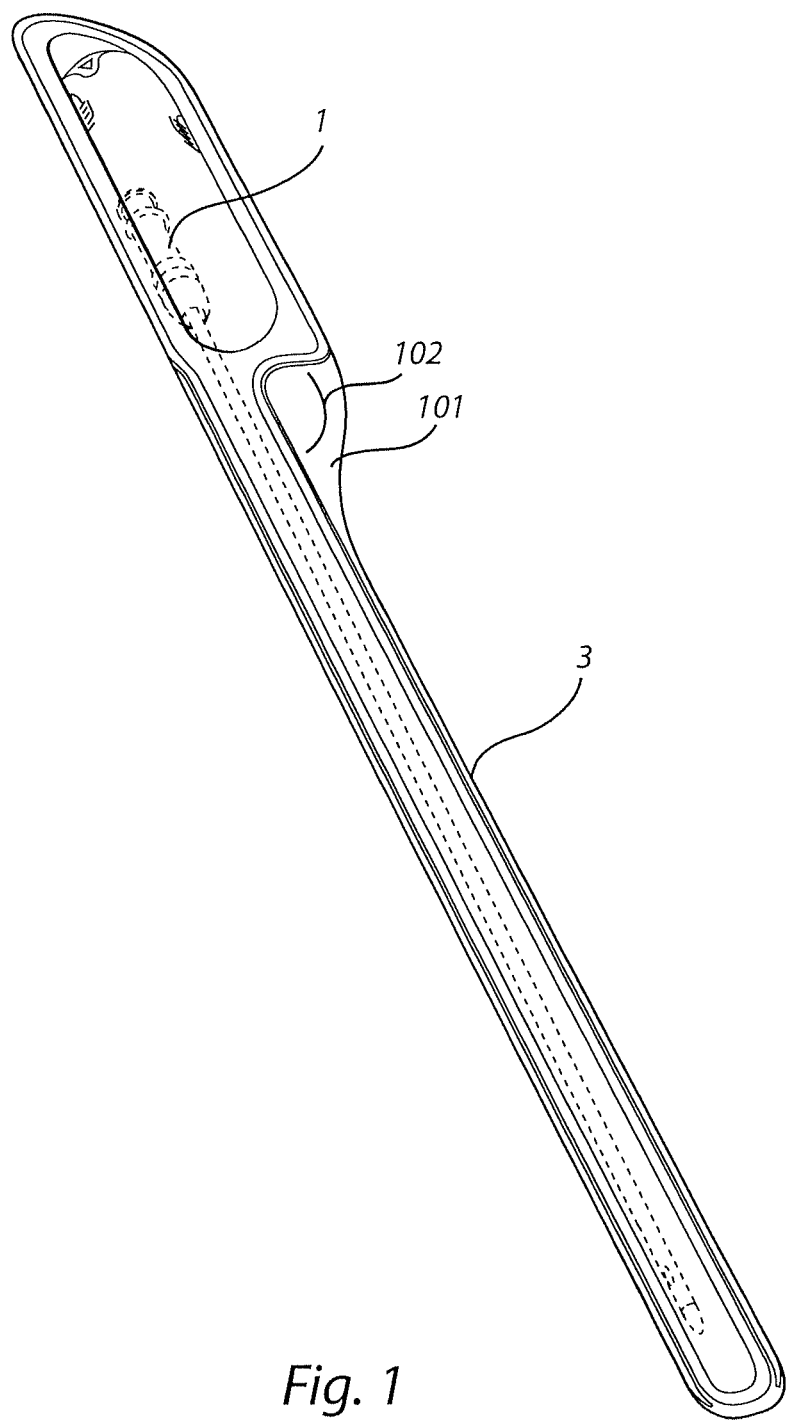
FIG. 1 illustrates a perspective view of a catheter assembly in accordance with an embodiment of the present invention.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, etc.

Catheters may be used for many different purposes, and for insertion into various types of body-cavities. However, the following discussion is in particular concerned with the preferred field of use, hydrophilic urinary catheters, even though the invention is not limited to this particular type of catheters, and may also be used for non-hydrophilic urinary catheters.

Figure 2:
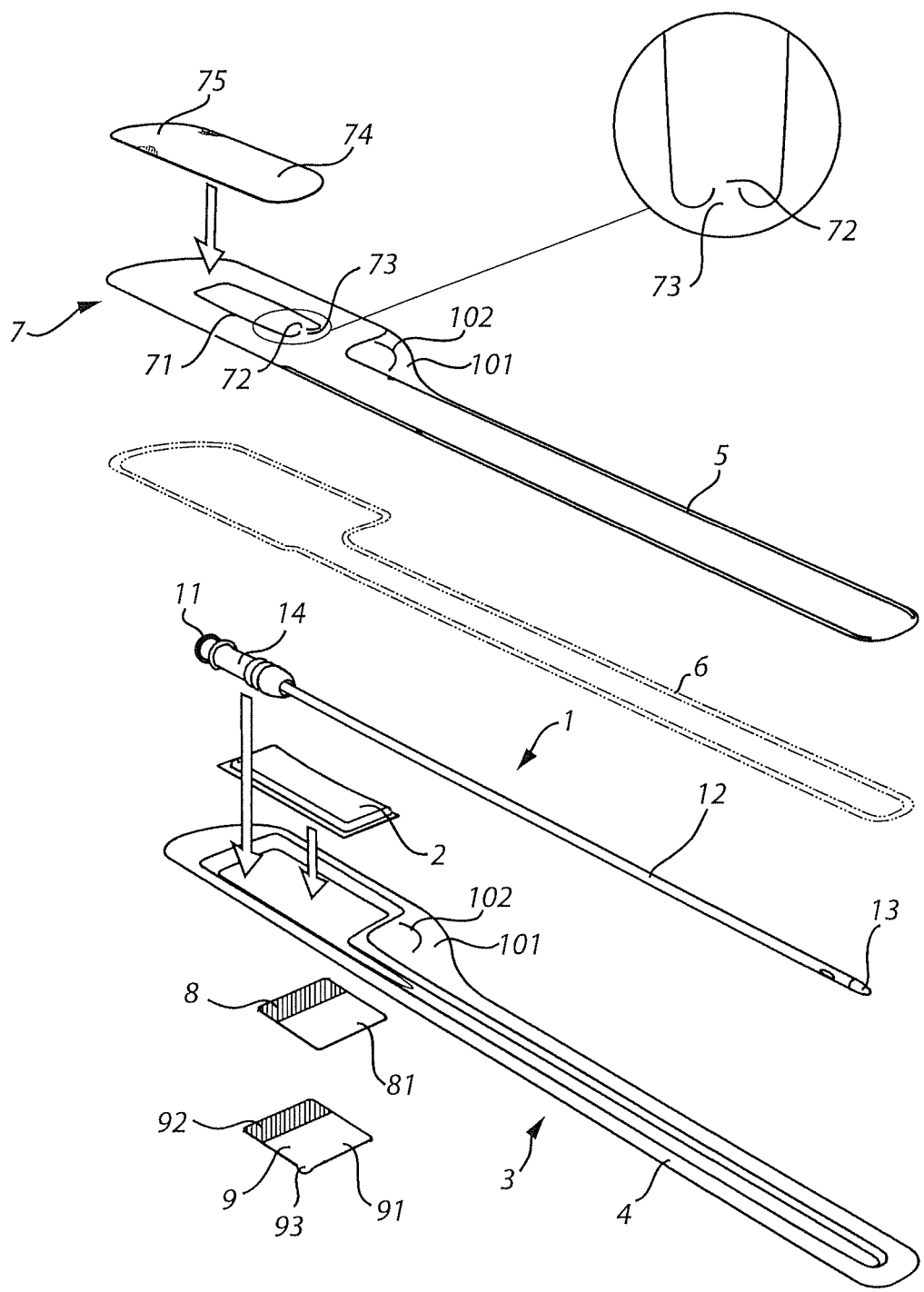
FIG. 2 illustrates an exploded view of the catheter assembly in FIG. 1.

The catheter assembly as illustrated in FIGS. 1-2 comprises a catheter 1 having a hydrophilic surface coating, a wetting fluid for activation of said hydrophilic surface coating and a package 3 accommodating the catheter and the wetting fluid.

The catheter 1 may be any type of hydrophilic catheter, as is per se well known in the art. Preferably, the catheter comprises a flared rearward portion, forming a flared connector 11, and an elongated shaft 12, connected to the flared connector 11, and in the opposite end having a catheter insertion end 13.

An applicator 14, in the form of e.g. a tube, sleeve or cuff, may be releasably attached to the connector 11, in order to be release from the connector prior to insertion, and to aid in manipulating the catheter during insertion without directly contacting the catheter surface.

At least a part of the elongate shaft 12 forms an insertable length to be inserted through a body opening of the user, such as the urethra in case of a urinary catheter. By insertable length is normally, in the context of a hydrophilic catheter, meant that length of the elongate shaft 12 which is coated with a hydrophilic material, for example PVP, or made of a hydrophilic material, and which is insertable into the urethra of the patient. Typically, this will be 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The coating may also comprise an osmolality-increasing compound, as is e.g. taught in EP 0 217 771

The wetting fluid is preferably arranged separate from the catheter, in a wetting fluid container 2, such as a pouch or a sachet. The wetting fluid container is openable by means of e.g. exerting a pressure to the container, whereby the wetting fluid is released into the package, thereby wetting the hydrophilic surface of the catheter. The wetting fluid is preferably a liquid, and most preferably an aqueous liquid, such as water or saline. Such wetting fluid containers and wetting fluids are per se well known in the art.

The flexible material used for wetting fluid pouch is preferably a flexible material which provides a moisture barrier or low water vapor transmission. The flexible material may e.g. comprise or consist of one or several of aluminum, aluminum oxide, silicone oxide, metallocene polyvinylidene chloride (PVdC) and poly(ethylene-vinylalochol) (EVOH). For example, the flexible material can be made as coextruded polyolefines with polyamides, poly(ethylene terephthalate) (PET), including barrier resins such as polyvinylidene chloride (PVdC) or polyethylene-vinylalcohol) (EVOH). However, other materials exhibiting similar properties are also feasible.

The wetting fluid may be any fluid that wets a hydrophilic surface of the catheter.

Preferably, the wetting fluid container 2 is arranged close to, and most preferably overlying, the connector end of the catheter.

The package comprises a first sheet material 4 and a second sheet material 5, connected around the edges to form an inner cavity housing the catheter and the wetting fluid. The first and second sheet materials are preferably connected around the edges by means of welding, forming a welded edge joint 6. Preferably, the first and second sheet materials comprise laminated sheets, having a weldable inner layer and a protective outer layer.

The sheet materials are preferably of a flexible plastics material. The material may be transparent, but opaque or semi-opaque materials may also be used. For example, the sheets can be made of polymer materials such as polyethene (PE), polypropylene (PP), polyamide (PA), poly(ethylene terephthalate) (PET), oriented polypropylene (OPP), oriented polyamide (OPA), etc. Also, the receptacle can be made from a laminate of such polymer materials and/or aluminum, aluminum oxide or other materials functioning as barrier materials.

The first sheet material 4 is preferably deep drawn into a trough shape, thereby forming an upper rim, to be in contact with the second sheet material 5, and a lower middle section, formed to accommodate the catheter and the wetting fluid sachet. The rim is preferably provided with an essentially planar edge surrounding the lowered middle section. The planar edge may have any dimensions, such as being very thin or being relatively wide. Further, the planar edge may have various dimensions around the circumference. The second sheet material 5 is preferably essentially planar, or only slightly curved.

The second sheet material 5 comprises a resealable opening 7. The resealable opening preferably comprises a perforation line 71 in the second sheet material, extending along a non-closed loop defining a flap opening. The non-closed loop defining the flap opening is preferably arranged over the connector end of the catheter 1. Further, the non-closed loop preferably has an opening 72 debouching towards the end of the package housing the insertion end of the catheter. At the end, the non-closed loop preferably forms a tongue 73 directed inwardly towards the non-closed opening of the non-closed loop. The loop ends, at the opening 72, are preferably directed towards the interior of the non-closed loop.

The non-closed loop generally forms a C- or U-shape.

The reseablable opening further preferably comprises a third sheet material 74, arranged over the non-closed loop, and connected to the second sheet material 5 by means of an adhesive. The third sheet material is preferably arranged to cover the entire flap opening with a margin, preferably exceeding 2 mm, and most preferably exceeding 5 mm. An end of the third sheet material is not adhered to the first sheet material, and forms a tab 75 providing a grip portion for peel opening of the package. The tab is preferably arranged in the end directed towards the insertable part of the catheter. Further, the tab may be provided with gripping means to facilitate gripping of the tab. The gripping means may e.g. be one or several of a surface coating, surface roughening, corrugations, embossment, perforations or a larger gripping opening, etc.

The adhesive is adapted to maintain a sterile closure of the package before use, and to be resealable after use. The adhesive preferably has a strength to withstand a pulling force in the range of 3-10 N. The adhesive can e.g. be an acrylate emulsion, or an acrylate based hot melt adhesive.

The third sheet material further preferably comprises a weakened area forming a seal integrity mark. Hereby, it is ensured that the seal has not been broken before use, ensuring full integrity of the product. Preferably, the seal integrity mark is arranged between the tab and the part of the third sheet material overlying the perforation line. The weakened area preferably comprises weakened or perforated lines arranged in a pattern, e.g. as illustrated in the drawings, making part of the third sheet material to remain adhered to the first sheet material during peel off of the third sheet material.

The catheter assembly may further comprise a fourth sheet material 8 arranged on the first sheet material, i.e. on the side of the package being opposed to the third sheet material and the resealable opening. The fourth sheet material is also connected by means of an adhesive to the package, and forms a tab 81 not provided with adhesive, said tab providing a grip portion for exposure of said adhesive to form a holding arrangement for the package. By means of this fourth sheet material, the catheter assembly may e.g. be attached to a sink, a wall or the like, which enables very efficient and easy handling of the product, even for user with reduced dexterity.

In order to ensure that the fourth sheet materials are not removed completely during peeling, perforated lines (not shown) may be arranged on one or preferably both of the sides. The perforated lines preferably extend from the outer side of the fourth sheet material, about in the center of the sheet material, towards the interior of the sheet in a direction away from the pulling tab. The tear line preferably ends in a hook or the like towards the side of the sheet, but not extending entirely to the side of the sheet.

Alternatively, the fourth sheet may comprise two separate sheets: An inner sheet 8, which is connected to the first sheet by means of e.g. adhesive, and an outer sheet 9, which is connected to the inner sheet. The connection between the inner and outer sheet may also be provided by means of adhesive. The adhesive may be provided on either the outer surface of the inner sheet or the inner surface of the outer sheet, or preferably on both. A tab 93 is provided in the outer sheet to allow for simple separation of the inner and outer sheets. In an area 92 opposite the tab 93, the connection between the inner and outer sheets is made stronger, e.g. by using a stronger adhesive. Hereby, separation of the two sheets, which is initiated by pulling the tab 93, is stopped at this area 92, and the exposed areas with adhesive on the inner and/or outer sheets may be used to attach the package to any suitable surface or object.

The third and fourth sheet materials may e.g. be of polypropene (polypropylene), polyester or polyethene (polyethylene).

In a preferred embodiment, the package is elongate, and preferably has an essentially rectangular forward part, in the form of an elongate pocket, and an enlarged rearward part. The enlarged rearward part may be rectangular or of other shapes, such as having rounded corners, etc. The enlarged rearward part is preferably dimensioned to accommodate the catheter connector and the wetting fluid container. The elongate pocket is preferably dimensioned to accommodate, and narrowly surround, the insertable part of the catheter. Hereby, a very compact product is obtained.

For enabling folding of the catheter into a more compact state, there is further provided an insert opening, arranged to enable reception of an end of the package therein.

In the illustrative example, the insert opening is formed on a tab area 101 formed in the first and second foil materials 4, 5. The tab area extends out from the inner compartment formed by the foils. In the tab area, a slit opening 102 is formed, e.g. by cutting the material.

The slit opening forms a line opening. This line may be straight, but preferably, the line is slightly curved, thereby making insertion through the slit opening simpler. Preferably, the line comprises ends being arranged closer to the inner compartment of the package and the catheter than the intermediate convex portion.

However, the insert opening may also be formed in other shapes. For example, the insert opening may comprise a hole, e.g. having a circular, oval or rectangular shape. Still further, the insert opening may be formed as an open-ended pocket by providing an additional layer of material, or by folding the material of any of the foils. Further, the insert opening may be formed as a strap, being connected to the sides of the package, but with an unattached loop there between, forming the insert opening. The insert opening may also comprise a strap or tape encircling the package.

Although the wetting fluid in the described embodiments has been arranged separated from the catheter, in a wetting fluid container, it is also possible to arrange the wetting fluid in direct contact with the catheter, thereby always maintaining a ready-to-use state. Further, if a wetting fluid container is used, it is possible to arrange this container close to the connector end of the catheter, close to the insertion end of the catheter, or at any other location within the receptacle.

Further, the package may be formed in other ways. For example, the package may be formed, entirely or partly, by a tube, or by a single, folded foil material. Also, the shape of the package may vary, and e.g. the package may have a uniform width along the package.

In order to provide a narrow surrounding for the catheter, the inner compartment formed in the package preferably has an internal diameter only slightly larger than an outer diameter of the catheter. The term "narrow surrounding" is, in the context of this application, to be understood in a broad sense, meaning that the diameter of the tubular member essentially matches that of the catheter, with a difference between the two sufficient enough to enable fluid to surround the catheter meanwhile not being excessive. The diameter difference may for instance be in the range 0.5 to 10 mm, more preferred in the range 0.5 to 5 mm, and most preferred in the range 0.5 to 2 mm.

The process of folding of the catheter assembly into a folded, compact state will now be discussed in somewhat more detail, with reference to FIGS. 3A-D.

Figure 3A:
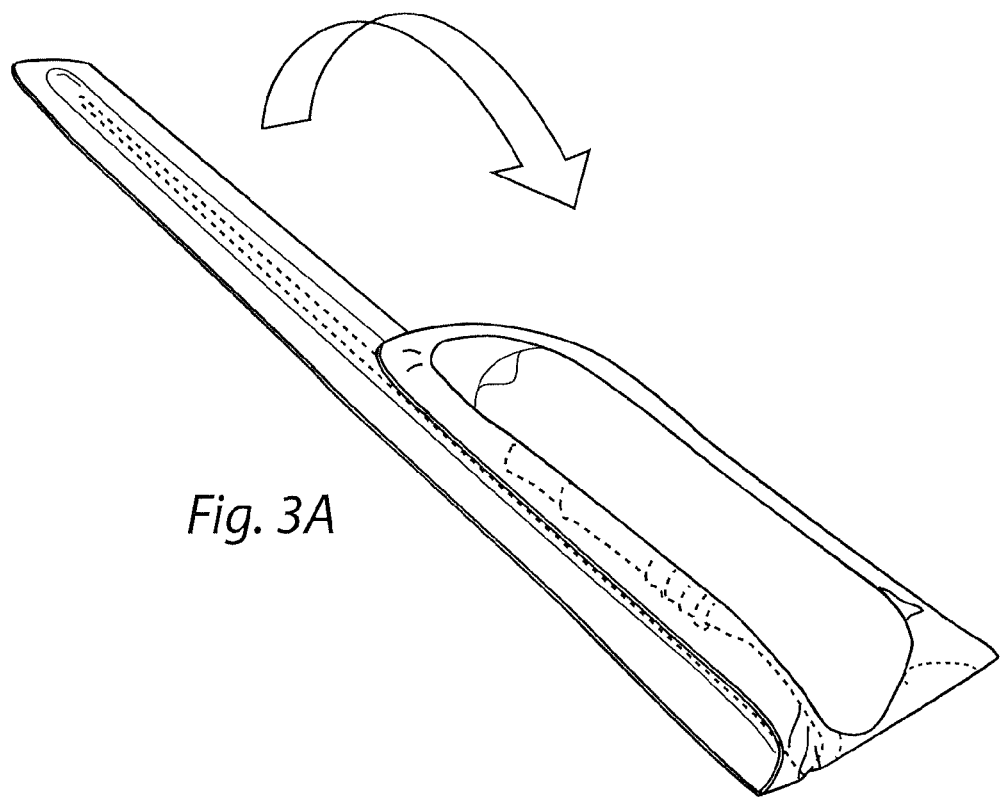
FIG. 3A-D illustrate folding of the catheter assembly of FIG. 1 into a three times folded state, where
Figure 3B:
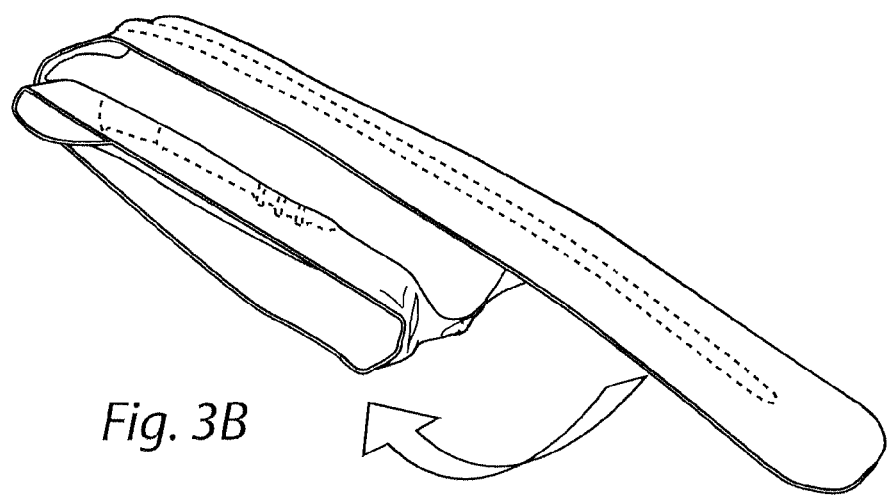

In a first step, the catheter assembly is folded close to the end of the wetting fluid container, as is illustrated in FIG. 3A. Thereafter, the forward end of the package is folded again, around the wetting fluid container, as illustrated in FIG. 3B. Finally, the remaining forward end of the package is folded again around the wetting fluid compartment, and inserted through the insert opening. Hereby, the elasticity of the package and the catheter, and the friction between the surfaces, maintains the catheter assembly in this folded state. Further, releasing the folded state is just as simple. By removing the inserted end, the catheter assembly by itself unfolds to the natural, straight state.

Figure 3C:
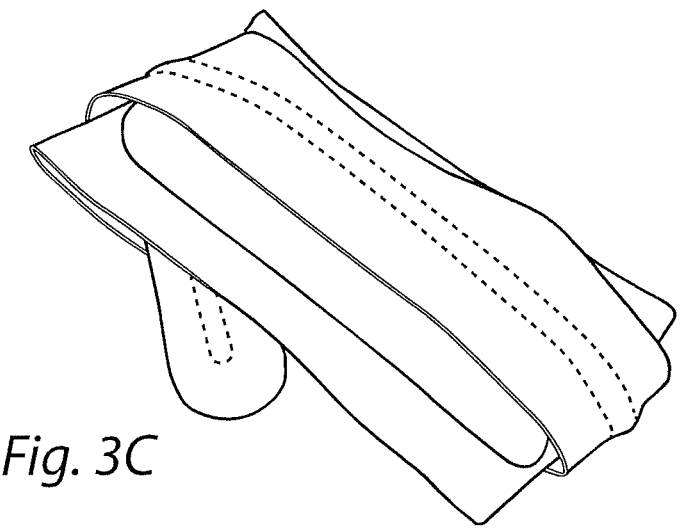
Figure 3D:
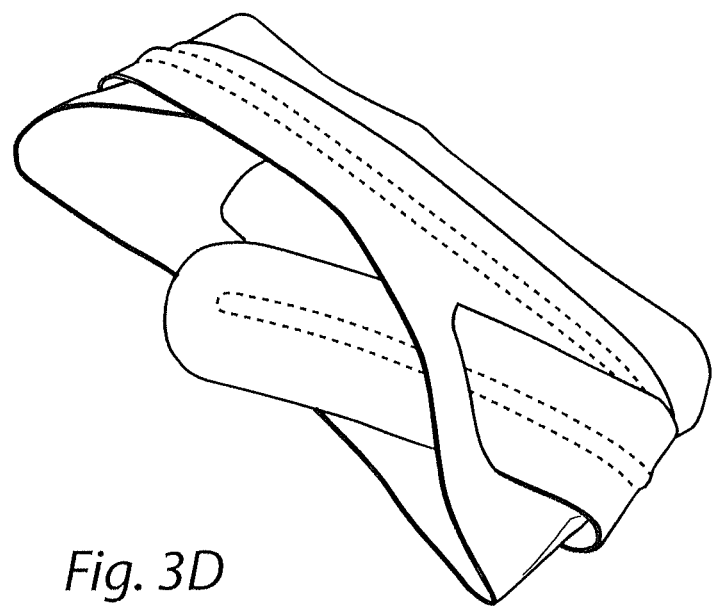

The hereby obtained three times folded state is illustrated in FIGS. 3C and 3D. As is clearly seen from these figures, the length of the catheter assembly in this state is less than a third of the length of the catheter assembly in its natural, unfolded state.

Figure 4:
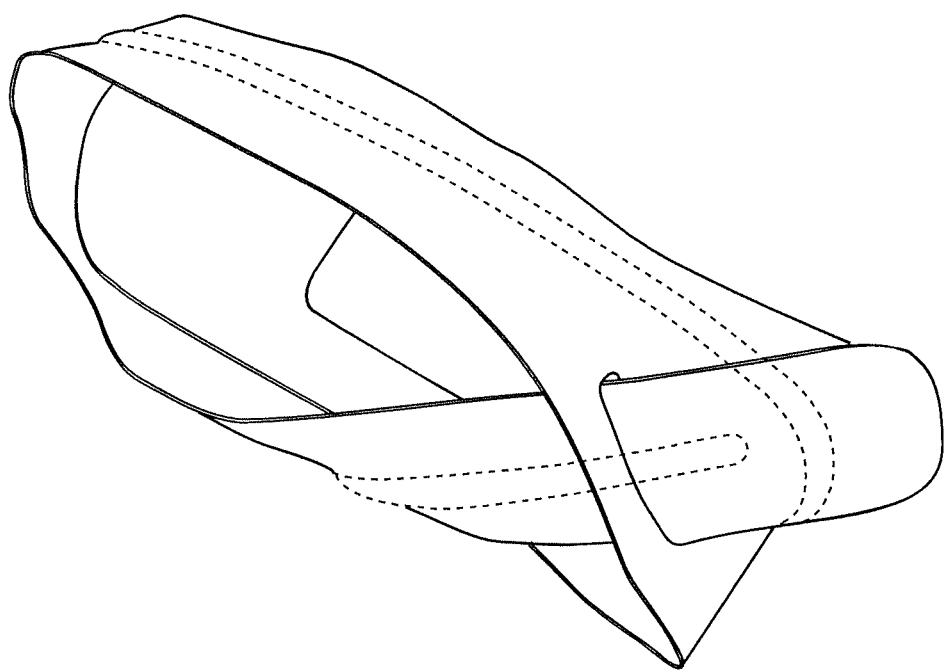
FIG. 4 illustrates the catheter assembly of FIG. 1 as folded in an alternative way, in which the catheter assembly assumes a two times folded state.

However, it is also possible to fold the catheter assembly only twice. This is illustrated in FIG. 4, where the package has been folded two times, generally corresponding to the first two folding steps discussed above with reference to FIG. 3. However, in this twice folded state, the forward end of the package is then directly inserted through the insert opening, without any further folding. In this state, the folded catheter assembly is slightly larger than in the above-discussed thrice folded state. However, even in this state, the length of the catheter assembly only slightly exceeds a third of the length of the catheter assembly in its natural, unfolded state, and is significantly shorter than half this length.

A further option is to fold the catheter assembly only once, whereby the catheter assembly may be folded close to the middle, and the forward end then be directly inserted through the insert opening in the above-discussed manner. Hereby, a catheter assembly having about half the length of the natural, unfolded catheter assembly will be obtained. Folding of the catheter assembly more than three times would naturally also be feasible, in order to obtain an even further compacted product.

In use, the user may, as a preparation for bringing the catheter assembly along with him, fold the catheter assembly into the desired compacted state, and store the catheter assembly in a pocket, in a hand bag, or in any other suitable location. When the catheter is to be used, the catheter assembly is unfolded, and the wetting fluid container is opened, for activation of the hydrophilic surface of the catheter. After sufficient wetting, the tab of the fourth sheet may be peeled, so that the catheter assembly can be connected to a sink or the like. The tab of the third sheet is peeled open, and the catheter is removed and used. Thereafter, the catheter may be re-inserted, and the package can then be closed with the resealable opening, and stored for later disposal. It is also possible to again re-arrange the catheter in a folded, compact disposition after use, which makes disposal of the catheter assembly in a discreet manner even simpler.

A method of manufacturing the above-discussed catheter assembly preferably comprises the following steps of producing the package, performed in any order: providing a first and second sheet material; deep drawing the first sheet into the appropriate trough shape; providing a resealable opening, e.g. by the sub-steps of: providing the non-closed loop perforated line in the second sheet material by cutting the material; providing third sheet materials; optionally, providing the perforated lines in the third sheet material; adhering the third sheet material to the first sheet material; connecting the first and second sheet material to each other along the edges, e.g. by means of welding; optionally, providing a hanging means, e.g. in the form of an adhesive, which may include the sub-steps: providing the one or several sheet(s) of fourth sheet material; optionally, providing the perforated lines in the fourth sheet material; and adhering the fourth sheet material to the second sheet material; and/or forming, before or after any of the other steps, an insert opening for receiving an end of the catheter package in a folded state. The insert opening may e.g. be obtained by cutting a slit opening in a tab area of the package.

In addition, the catheters and the wetting fluid container is provided and arranged within the package before the package is finally closed, and sterilization of the product is provided by means of e.g. radiation.

Specific embodiments of the invention have now been described. However, several alternatives are possible, as would be apparent for someone skilled in the art. For example, although the wetting fluid in the described embodiments has been arranged separated from the catheter, in a wetting fluid container, it is also possible to arrange the wetting fluid in direct contact with the catheter, thereby always maintaining a ready-to-use state. Further, if a wetting fluid container is used, it is possible to arrange this container close to the connector end of the catheter, close to the insertion end of the catheter, or at any other location within the receptacle. Further, the package may be produced in other ways. For example, the package may be formed, entirely or partly, by a tube, or by a single, folded foil material. Also, the shape of the package may vary, and e.g. the package may have a uniform width along the package. Still further, resealable openings may be provided in other forms than in the above-indicated preferred embodiment. The catheter assembly may also be used without any resealable opening, and may e.g. be opened by peeling the package open at an end, or by tearing the package open at any desired location. Further, a package without the fourth sheet is feasible, and other sheets may also be used. Further, other shapes for the various perforation lines are feasible. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A catheter assembly comprising an intermittent urinary catheter and an elongate package accommodating said intermittent urinary catheter in a closed condition, wherein the package is provided with an insert opening arranged to releasably receive and completely surround an end of the elongate package in said closed condition to temporarily retain said elongate package in a folded disposition in which also the intermittent urinary catheter is folded, wherein the assembly further comprises a wetting fluid for activation of said hydrophilic surface coating, said wetting fluid being accommodated by said package.

2. The catheter assembly of claim 1, wherein the insert opening is formed as a slit opening with closed ends in the package.

3. The catheter assembly of claim 2, wherein the slit opening is formed in a tab area on a side of said package.

4. The catheter assembly of claim 1, wherein the insert opening is dimensioned to narrowly surround a received end of the package.

5. The catheter assembly of claim 1, wherein the package is formed of two sheets of foil material being joined along the edges of the foils, thereby forming a closed compartment therein for housing said catheter.

6. The catheter assembly of claim 5, wherein the insert opening is arranged in a part of the package not forming said compartment.

7. The catheter assembly of claim 1, wherein the insert opening is arranged at, or close to, the part of the package housing the non-insertable, rearward end of the catheter.

8. The catheter assembly of claim 1, wherein the wetting fluid is arranged separated from said catheter in said package, and being arranged in a wetting fluid container arranged within said package, and wherein the insert opening is arranged in the vicinity of said wetting fluid container.

9. The catheter assembly of claim 1, wherein the closed package in its folded disposition comprises at least one fold.

10. The catheter assembly of claim 1, wherein in the folded disposition, a maximum length of said catheter assembly is less than half a length of said catheter in a straight disposition.

11. The catheter assembly of claim 1, wherein the length of said catheter exceeds 200 mm, and exceeds 300 mm.

12. The catheter assembly of claim 1, wherein in folded disposition, the package is folded at least once such that a forward end of the package is directly inserted through the insert opening, thereby providing a compact assembly that may be stored.

13. The catheter assembly of claim 1, wherein the closed package in folded disposition comprises at least two folds.

14. The catheter assembly of claim 1, wherein the closed package in folded disposition comprises at least three folds.

15. The catheter assembly of claim 1, wherein in folded disposition, a maximum length of said catheter assembly is less than a third of a length of said catheter in a straight disposition.

16. The catheter assembly of claim 1, wherein the insert opening is formed as a slit opening with closed ends in the package, said slit opening forming a line.

17. The catheter assembly of claim 16, wherein the line is curved.

18. The catheter assembly of claim 1, wherein the insert opening comprises a hole having a circular, oval or rectangular shape.

19. A catheter assembly comprising an intermittent urinary catheter and an elongate package accommodating said intermittent urinary catheter in a closed condition, wherein the package is provided with an insert opening arranged to releasably receive and completely surround an end of the elongate package in said closed condition to temporarily retain said elongate package in a folded disposition in which also the intermittent urinary catheter is folded, wherein the package is formed of two sheets of foil material being joined along the edges of the foils, thereby forming a closed compartment therein for housing said catheter.

20. The catheter assembly of claim 19, wherein the insert opening is arranged in a part of the package not forming said compartment.

* * * * *